(12) United States Patent
Roussin et al.

(10) Patent No.: US 6,171,615 B1
(45) Date of Patent: Jan. 9, 2001

(54) SUSTAINED RELEASE THEOPHYLLINE FORMULATIONS, EXCIPIENT SYSTEMS AND METHODS OF PRODUCTION

(75) Inventors: Pascale Roussin, Paris (FR); Sarma Duddu, San Carlos, CA (US)

(73) Assignees: Gattefossé, Saint Priest (FR); SmithKline Beecham Corp., Philadelphia, PA (US)

(*) Notice: Under 35 U.S.C. 154(b), the term of this patent shall be extended for 0 days.

(21) Appl. No.: 09/110,599

(22) Filed: Jul. 6, 1998

(51) Int. Cl.[7] ....................................................... A61K 9/52
(52) U.S. Cl. ............................ 424/457; 424/486; 424/452
(58) Field of Search ........................................ 424/486, 452, 424/456–57; 514/826, 962, 965, 970

(56) References Cited

U.S. PATENT DOCUMENTS

| | | |
|---|---|---|
| 2,538,127 | 1/1951 | Saunders et al. . |
| 3,374,146 | 3/1968 | Blicharz et al. . |
| 4,454,113 | 6/1984 | Hemker . |
| 4,755,389 | 7/1988 | Jones et al. . |
| 4,777,048 | 10/1988 | Hersh et al. . |
| 4,797,286 | 1/1989 | Thakkar et al. . |
| 4,880,634 | 11/1989 | Speiser . |
| 4,988,679 | 1/1991 | Chavkin et al. . |
| 5,188,838 | 2/1993 | Deleuil et al. . |
| 5,288,505 | 2/1994 | Deboeck et al. . |
| 5,368,861 | 11/1994 | Ushimaru et al. . |
| 5,371,109 | 12/1994 | Engstrom et al. . |
| 5,433,951 | 7/1995 | Serajuddin et al. . |
| 5,436,230 | 7/1995 | Soudant et al. . |
| 5,567,439 | 10/1996 | Myers et al. . |
| 5,863,545 | * 1/1999 | Griat . |

OTHER PUBLICATIONS

*Modelling of Theophylline Compound Released from Hard Gelatin Capsules Containing Gelucire Matrix Granules*, Drug Development and Industrial Pharmacy, 17(10), 1267–1277 (1991).

"*The Physical Characterisation of Complex Glyceride Mixtures*", Sutananta, Chapter 5, The School of Pharmacy, University of London, Mar., 1993.

* cited by examiner

Primary Examiner—Edward J. Webman
(74) Attorney, Agent, or Firm—Norris, McLaughlin & Marcus

(57) ABSTRACT

A stable sustained release theophylline formulation is prepared by incorporating theophylline into a semi-solid matrix comprising polyglycolized glycerides (GELUCIRE® excipient) and a mixture of nucleation enhancers. Theophylline is admixed with molten GELUCIRE to make the sustained release formulation. The nucleation enhancer composition is then incorporated in the admixture to make the sustained release formulation resistant to changes in dissolution upon aging. Orally administrable compositions are prepared by filling gelatin capsules with the formulation. The polyglycolized glycerides (GELUCIRE) and the nucleation enhancer composition also can be used as an excipient system for preparing sustained release pharmaceutical compositions.

6 Claims, 10 Drawing Sheets

DRS of Gelucire Form I

SUSTAINED RELEASE THEOPHYLLINE FORMULATIONS, EXCIPIENT SYSTEMS AND METHODS OF PRODUCTION

BACKGROUND OF THE INVENTION

1. Field of the Invention

The present invention relates to sustained release pharmaceutical compositions. More particularly, the invention has to do with a method employing certain GELUCIRE® excipients, particularly GELUCIRE 50/13 and GELUCIRE 53/10, in combination with nucleation enhancers to stabilize an excipient system and to prepare a new sustained release theophylline formulation in capsule unit dosage form.

2. Description of Related Art

GELUCIRE, a product of Gattefossé s.a., Saint-Priest Cedex, France and Westwood, N.J., USA, is a well known excipient which is available with a range of properties and it is used in various applications including preparing sustained release pharmaceutical compositions, as described in the technical and patent literature. For example, U.S. Pat. No. 4,797,286 describes sustained release, orally administrable pharmaceutical formulations employing GELUCIRE to make a carrier matrix. The compositions were prepared by admixing a pharmaceutically active agent with molten GELUCIRE and then filling capsules with the admixture.

A sustained release formulation containing captopril is described in U.S. Pat. No. 5,433,951. Various GELUCIRE compositions were employed according to the experimental descriptions to make captopril formulations which were then used to fill hard gelatin capsules.

Sustained release compositions of theophylline are described in U.S. Pat. No. 4,988,679. In this case, triglycerides of a medium chain length alkanoic acid or distilled acetylated monoglycerides, a liquid, high HLB polyglyceryl ester and colloidal silicon dioxide were employed to make a liquid sustained release composition.

In a 1991 article, Brossard, C., et al., *Modelling of Theophylline Compound Release from Hard Gelatin Capsules Containing Gelucire Matrix Granules,* Drug Development and Industrial Pharmacy, 17(10), 1267–1277, the authors describe hard shell gelatin capsules containing four theophylline compounds of different solubilities (theophylline and the theophylline derivatives etofylline, diprophylline and proxyphylline) prepared with various GELUCIRE compositions. The theophylline and its derivatives were incorporated into the GELUCIRE compositions by a process of melting at 80° C., then congealing at 4° C. followed by granulation. Compritol® 888 glyceryl behenate, another product of Gattefossé, was used in combination with GELUCIRE to make the sustained release compositions. The authors found that the GELUCIRE compositions were effective in making timed release compositions of the theophylline derivatives, but in the case of theophylline itself the length of its needle-like crystals prevented effective inclusion of the drug in the fatty matrix of the GELUCIRE compositions and release of the theophylline was always faster than expected.

A more recent article, Sutananta, W., *The Physical Characterization of Complex Glyceride Mixtures,* School of Pharmacy, University of London, March 1993, describes the use of GELUCIRE compositions, including GELUCIRE 50/13, with theophylline. The author concluded that GELUCIRE 50/13 matrices were not effective to resolve problems associated with dissolution upon ageing.

We have now discovered a means of making effective sustained release pharmaceutical compositions of theophylline for delivery in a gelatin capsule by employing certain GELUCIRE excipients in combination with certain nucleation enhancers. The pharmaceutical compositions described in this study are particularly stable with respect to dissolution upon ageing.

All percentages and ratios set forth herein are expressed as weight/weight, unless otherwise specified.

SUMMARY OF THE INVENTION

The invention has to do with a sustained release system for pharmaceutically active agents, a process for stabilizing such systems and the sustained release pharmaceutical compositions thereby prepared. More specifically, the system employs GELUCIRE 50/13 in combination with certain nucleation enhancers which we have found to be particularly effective for preventing dissolution upon ageing in theophylline compositions.

GELUCIRE is a semi-solid excipient composed of fatty acid ($C_{12}$–$C_{18}$) esters of glycerol and polyethylene glycol esters ("PEG esters"). Theophylline is a well-known therapeutic agent for human and veterinary use and is described in the *Merck Index* as 3,7-dihydro-1,3-dimethyl-1H-purine-2,6-dione. For example, theophylline is a bronchodilator which can be used to treat symptomas from asthma in chronic bronchitis and emphysema.

In the process of making the stabilized pharmaceutical compositions, the GELUCIRE is melted with stirring followed by adding the active ingredient or drug while maintaining heating and stirring until the mixture is homogeneous. The nucleation enhancers are then added, maintaining the stirring and heating and the homogeneous mixture is filled into hard gelatin capsules.

DETAILED DESCRIPTION OF THE INVENTION

Figure 1:
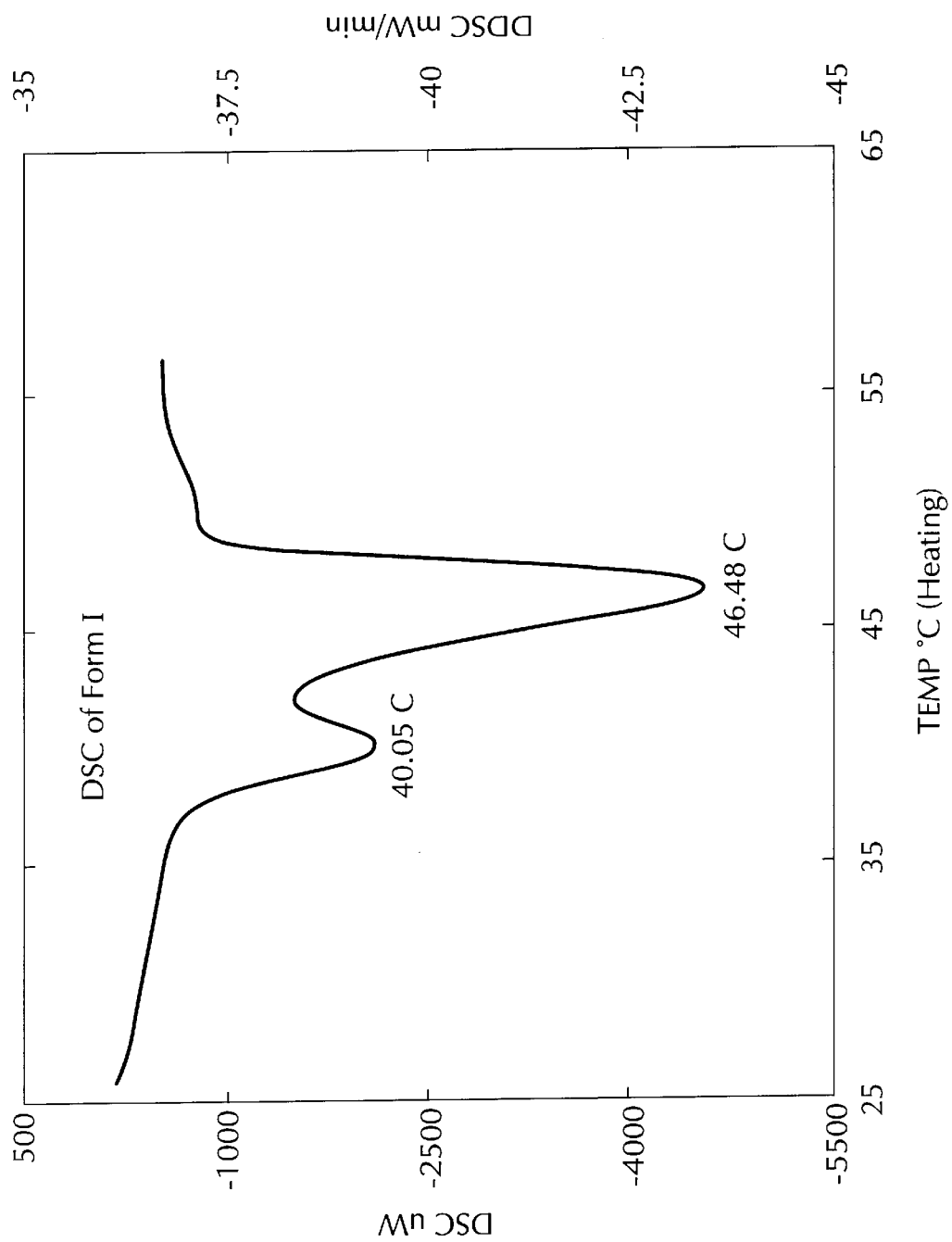
FIG. 1: DSC curve of GELUCIRE 50/13 form I.

The preparation of therapeutically effective, orally administrable, sustained release compositions of theophylline has been complicated because of problems associated with dissolution upon ageing. In some cases, when GELUCIRE based matrices are not effectively stabilized, the drug will dissolve more quickly after ageing due to a change in the physical structure and morphology of the material. We have now discovered that the use of a nucleation enhancer composition added to GELUCIRE 50/13 excipient can be used effectively to inhibit physical changes of GELUCIRE 50/13 and consequently decrease significantly dissolution changes upon ageing of highly water soluble pharmaceutical agents such as theophylline, particularly theophylline itself, and to prepare compositions for use in sustained release gelatin capsules.

The nucleation enhancer composition is comprised of glyceryl monostearate (GMS) and polyethylene glycol (PEG) having a number average molecular weight (abbreviated herein as "PM") of from about 1,000 to about 2,000, preferably about 1300–1600 and most preferably about 1450. The ratio of PEG to GMS in the composition can be varied from about 1:2 to about 2:1 and excellent results have been obtained when the ratio is from about 1.2:1 to about 1:1.2. The nucleation enhancer composition is employed in amounts from about 5% to about 50% by weight, preferably from about 5% to about 10% by weight of the GELUCIRE composition.

GELUCIRE compositions are inert semi-solid waxy materials which are amphiphilic in character and are available with varying physical characteristics. They are surface active in nature and disperse or solubilize in aqueous media forming micelles, microscopic globules or vesicles. They are identified by their melting point/HLB value. The melting point is expressed in degrees Celsius and the HLB (Hydrophile-Lipophile Balance) is a numerical scale extending from 0 to approximately 20. Lower HLB values denote more lipophilic and hydrophobic substances, and higher values denote more hydrophilic and lipophobic substances. The affinity of a compound for water or for oily substances is determined and its HLB value is assigned experimentally. One or a mixture of different grades of GELUCIRE excipient may be chosen to achieve the desired characteristics of melting point and/or HLB value.

As to the chemistry of GELUCIRE 50/13 compositions, they are polyglycolized glycerides that are prepared by the alcoholysis reaction of natural oils with polyethylene glycols (PEG). They are mixtures of monoesters, diesters and/or triesters of glycerides of long chain ($C_{12}$ to $C_{18}$) fatty acids, and PEG (mono- and/or di-) esters of long chain ($C_{12}$ to $C_{18}$) fatty acids and can include free PEG. GELUCIRE compositions are generally described herein as fatty acid esters of glycerol and PEG esters or as polyglycolized glycerides.

The large family of GELUCIRE compositions is characterized by a wide range of melting points of from about 33° C. to about 64° C. and most commonly from about 35° C. to about 55° C., and by a variety of HLB values of from about 1 to about 14, most commonly from about 7 to about 14. For example, GELUCIRE 50/13 designates a melting point of approximately 50° C. and an HLB value of about 13 to this grade of GELUCIRE. The appropriate choice of melting point/HLB value of a GELUCIRE or a mixture of GELUCIRE compositions will provide the delivery characteristics needed for a specific function, e.g., immediate release, sustained release, and the like. The low melting points of many of the solid GELUCIRE compositions provide a means of incorporating the pharmaceutically active ingredients in them at temperatures from about 0° C. to about 50° C. above their respective melting points, and then filling the melt (solution and/or dispersion) in hard gelatin capsules. The melt solidifies inside the capsules upon cooling to room temperature.

GELUCIRE 50/13 and GELUCIRE 53/10 can be used according to our invention, but GELUCIRE 50/13 has been found to be particularly effective. It is composed of fatty acid (majority of $C_{16}$ and $C_{18}$) esters of glycerol, PEG esters and free PEG.

According to the U.S. Pharmacopeia (USP) theophylline can be used as a bronchodilator for treatment of symptomas from asthma in chronic bronchitis and emphysema. The present invention is concerned with the oral administration of theophylline in therapeutically effective amounts (known to those skilled in the art) and in a sustained release oral dosage form.

The process of the invention requires melting the GELUCIRE and heating the molten GELUCIRE at a temperature from about 5° C. to about 50° C. above its melting point while stirring. For GELUCIRE 50/13, heating is at a temperature from about 55° C. to about 100° C., preferably from about 65° C. to about 75° C. The pharmaceutical agent then is admixed with the molten GELUCIRE to make a first admixture. The temperature is maintained during and following admixing, and stirring of the first admixture is continued for a sufficient amount of time to ensure that the admixture is homogeneous. The amount of time required to attain homogeneity will be apparent to those skilled in the art and for theophylline admixed with GELUCIRE 50/13 on a laboratory scale the time required was from 10 to 30 minutes.

The nucleation enhancer composition then is admixed with the first homogeneous admixture while maintaining heating at about 65° C. to make a second admixture. Stirring of the second admixture is continued for a sufficient amount of time at about 65° C., to ensure that the admixture is homogeneous, thus making a second homogeneous admixture. The amount of time required to attain homogeneity will be apparent to those skilled in the art and for theophylline admixed with GELUCIRE 50/13 and a nucleation enhancer composition comprised of PEG 1450 and GMS the time on a laboratory scale is from about 1 to about 15 minutes.

We have unexpectedly found that the sequence of steps is important in that the nucleation enhancer must be added after the GELUCIRE is admixed with the pharmaceutically active agent in order to attain the desired sustained release properties of the invention.

The second homogeneous admixture is then filled into hard gelatin capsules. Heating and mixing is continued up to the time the capsules are filled and after the capsules are filled they are allowed to return to ambient temperature.

In a formulation comprising 40% theophylline and 60% of a mixture containing 90% GELUCIRE, 5% GMS and 5% PEG 1450, the following is an example of a process that has been used successfully:

1. Melt 47.25 g of GELUCIRE 50/13 in a beaker on a heating plate to 65° C. with stirring.
2. Add 35 g of theophylline and wait for 30 minutes to make sure the mixture is homogenous. The heating temperature is still 65° C.
3. Add 2.62 g of solid GMS and 2.62 g of solid PEG 1450 at the same time in the mixture, with stirring.
4. Wait for 5 to 10 minutes to obtain a homogenous mixture.
5. Fill the capsules with about 300 mg of the mixture.
6. Maintain capsules at ambient temperature for about 8 hours to allow solidification and thermal equilibrium.

The invention can comprise, consist essentially of or consist of polyglycolized glycerides, a nucleation enhancer composition and theophylline, as described herein, and the nucleation enhancer composition can comprise, consist essentially of or consist of glyceride monostearate and polyethylene glycol, as described herein.

EXAMPLES

Solid dispersions of 20% and 40% theophylline were prepared with GELUCIRE 50/13 as carrier with or without the incorporation of PEG 1450 and GMS, each at a concentration of 5% w/w of GELUCIRE excipient.

Dispersions were stored under various conditions of temperature and humidity and dissolution rate in water, and physical characterizations were performed at regular intervals for a period of 2 months.

In dispersions without PEG 1450 and GMS, dissolution profiles exhibited a substantial increase with storage time and temperature. Physical characterization showed that this dissolution change was associated with physical and morphological change in GELUCIRE 50/13 as a result of thermally induced phase separation and crystallization. Understanding the relation between dissolution and phase separation enabled us to determine that the addition of PEG 1450 and GMS to a molten admixture of GELUCIRE and theophylline during cooling facilitates complete phase separation and crystallization during capsule manufacture.

The dissolution changes were significantly minimized for the dispersions using PEG 1450 and GMS.

Materials and Methods

Materials

Anhydrous theophylline (Sigma Chemical Company, St. Louis, Mo.) was used as the pharmaceutical agent.

GELUCIRE 50/13 was used as the semi solid matrix.

PEG 1450 (flakes NF, Union Carbide, Danbury, Conn.), glycerides monostearate (Spectrum Chemical Mfg., Corp., Gardena, Calif.), Stearate 1500 (Gattefossé s.a., France), behenic acids (Gattefossé s.a., France), polyvinylpyrrolidone (ISP Technologies Inc., Wayne, N.J.), carboxymethylcellulose (Aqualon) and Cab-O-Sil (SKB lot #13800-1) were used as additives.

Methods

Preparation of the capsules

Hard Gelatin capsules were prepared by a hand filling operation.

Formulation A: GELUCIRE 50/13 was melted at 65° C. on a hot plate, and 20% or 40% of anhydrous theophylline was incorporated, while stirring.

Formulation B.: GELUCIRE 50/13 was melted at 65° C. on a hot plate, and 20% or 40% anhydrous theophylline was incorporated, while stirring. 5% each of PEG 1450 and GMS relative to the weight of GELUCIRE excipient, were incorporated in the molten mixture at 65° C. Stirring was conducted for 10–15 minutes until the mixture was homogeneous.

Approximately 350 mg of each mixture, at 65° C., was filled using an Eppendorf repeat pipet into size #1 white opaque hard gelatin capsules. Capsules A (containing Formulation A) and capsules B (containing Formulation B) were kept at room temperature for 12 hours and stored under various conditions of temperature and relative humidity. Capsules B were annealed for 15 hours at 40° C.

Dissolution Studies

Dissolution testing on fresh and aged capsules were performed using a USP II (paddles) apparatus at 50 RPM in Milli-Q Water (a highly purified water—a grade commonly used for dissolutions) at 37° C. Samples were withdrawn at various time points and analyzed by UV spectrophotometry (Hewlett Packard 8452) at 271 nm for the concentration of dissolved theophylline.

Differential Scanning Calorimetry (DSC)

Samples (9–12 mg) in closed aluminum pans were heated at 2° C./min in a Seiko DSC 120 from 25° C. to 65° C.

Dielectric Relaxation Spectroscopy (DRS)

Powdered samples were scanned from 25° C. to 65° C. in the frequency range of 10 Hz to 1 kHz. The peak in tan δ, where δ is the phase angle shift, at any frequency is considered to be the transition temperature at that frequency.

Modulated DSC (MDSC)

Reversing and non-reversing heat flow measurements were carried out using TA 2100 modulated DSC (from TA Instrument, Delaware, U.S.A.) at a heating rate of 2 C/min., 0.3 degrees amplitude and a 60 second period. While the heat flow was measured using a principle similar to that in a conventional DSC, the heat capacity or the reversing signal was measured independently from the total heat flow dependence on the temperature modulations.

Hot-Stage Microscopy

Samples suspended in silicone oil were heated at 2° C./min. and observed using polarizing microscopy while being heated. Changes in the morphology and the birefringence pattern were noted as a function of temperature.

Powder X-ray Diffractometry

Samples were exposed to CuKα radiation (45 kV×30 mA) in a wide angle X-ray diffractometer (Siemens D500) operated in a step-scan mode, with increments of 0.05°2θ.

Scanning Electron Microscopy (SEM)

Micrographs were obtained on a AMREY 1200 C Scanning Electron Microscope. Samples were coated with gold and SEMs were obtained at 15 kV.

Results and Discussion

Melting GELUCIRE 50/13 at 65° C. and holding for 30 minutes, followed by cooling at various rates ranging from 0.5 to 200° C./min. has produced materials which exhibit two distinctly different thermal behaviors as observed in a DSC. The solid forms associated with these two DSC curves are designated Forms I and II. Adding 20% or 40% w/w of theophylline did not affect the DSC curves in the temperature range 25° C. to 65° C. The DSC curves with and without theophylline were virtually superimposable, suggesting that perhaps there is no interaction between the drug and GELUCIRE 50/13.

Cooling GELUCIRE 50/13 or GELUCIRE 50/13-theophylline mixture from a molten state under ambient conditions to Room Temperature (RT) typically produced GELUCIRE 50/13 in form II. When stored for 2–3 hours at room temperature, form II was found to convert to form I. Thus, after the capsules were manufactured and the dissolution experiments were carried out on the capsules, the GELUCIRE was present in form I. Therefore, the solid form of interest in addressing the aging related changes in the dissolution of theophylline from GELUCIRE 50/13 matrix is form I.

Figure 2:
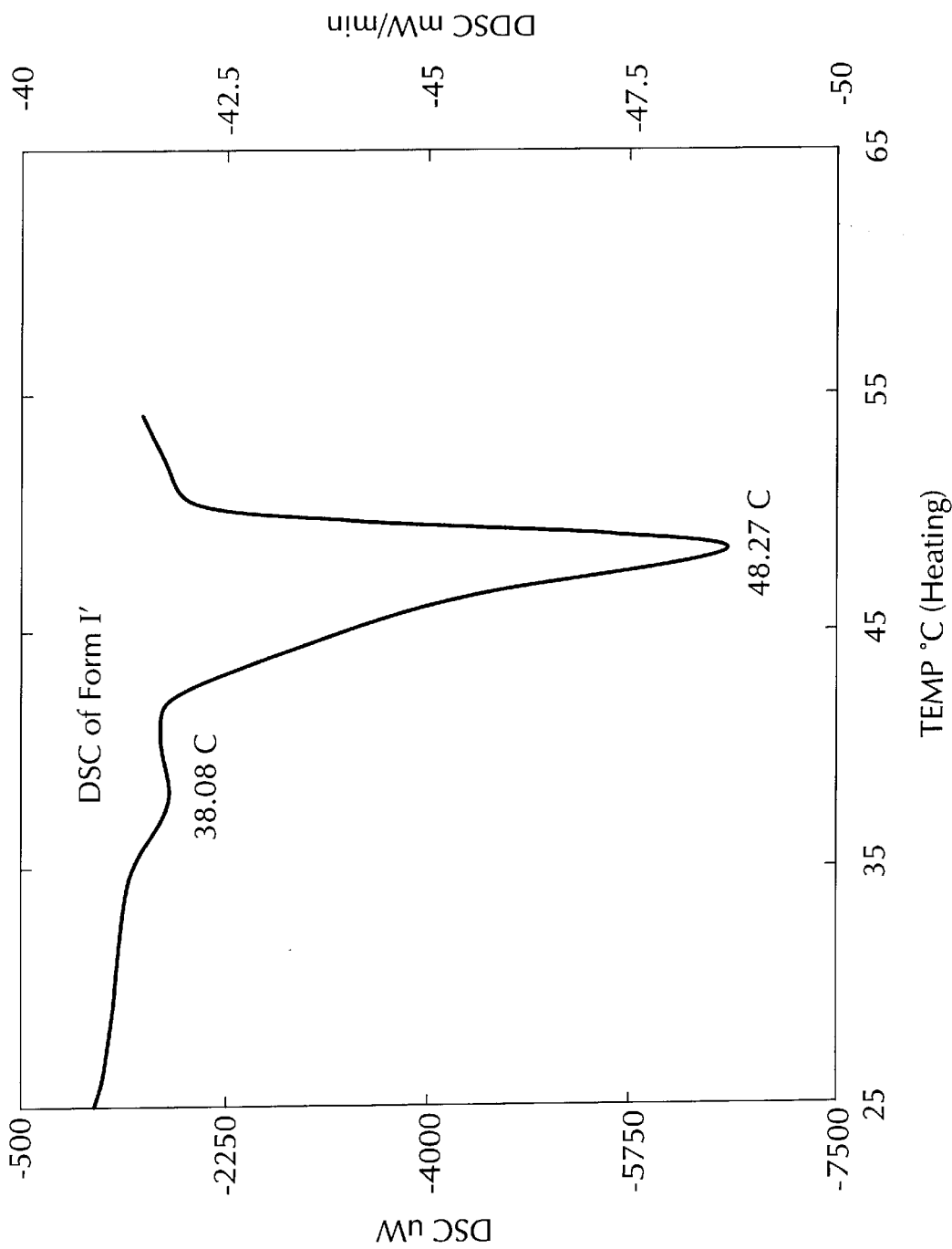
FIG. 2: DSC curve of GELUCIRE 50/13 form I'.
Figure 3:
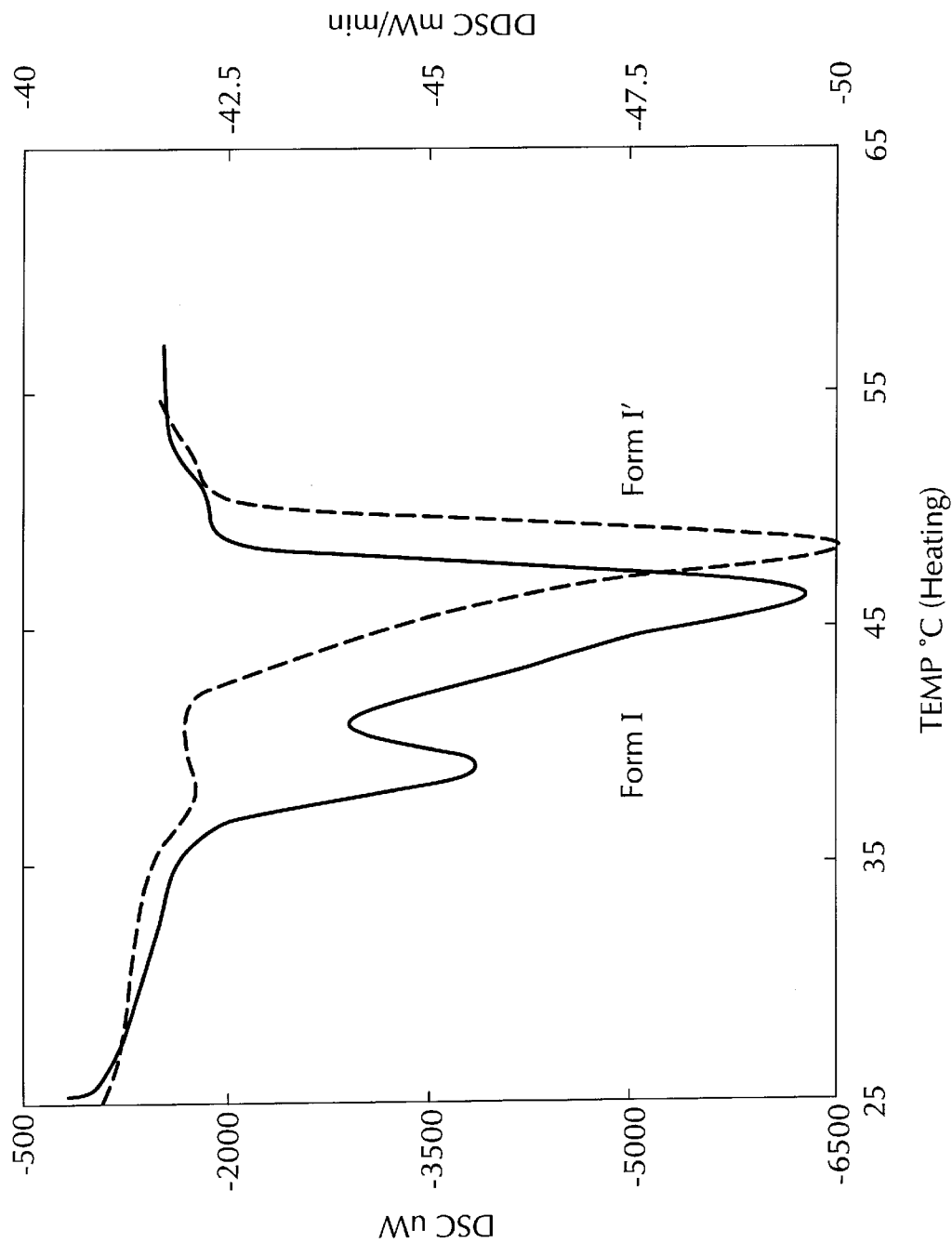
FIG. 3: DSC curves of GELUCIRE 50/13 forms I and I' showing the differences in their thermal behavior.
Figure 4:
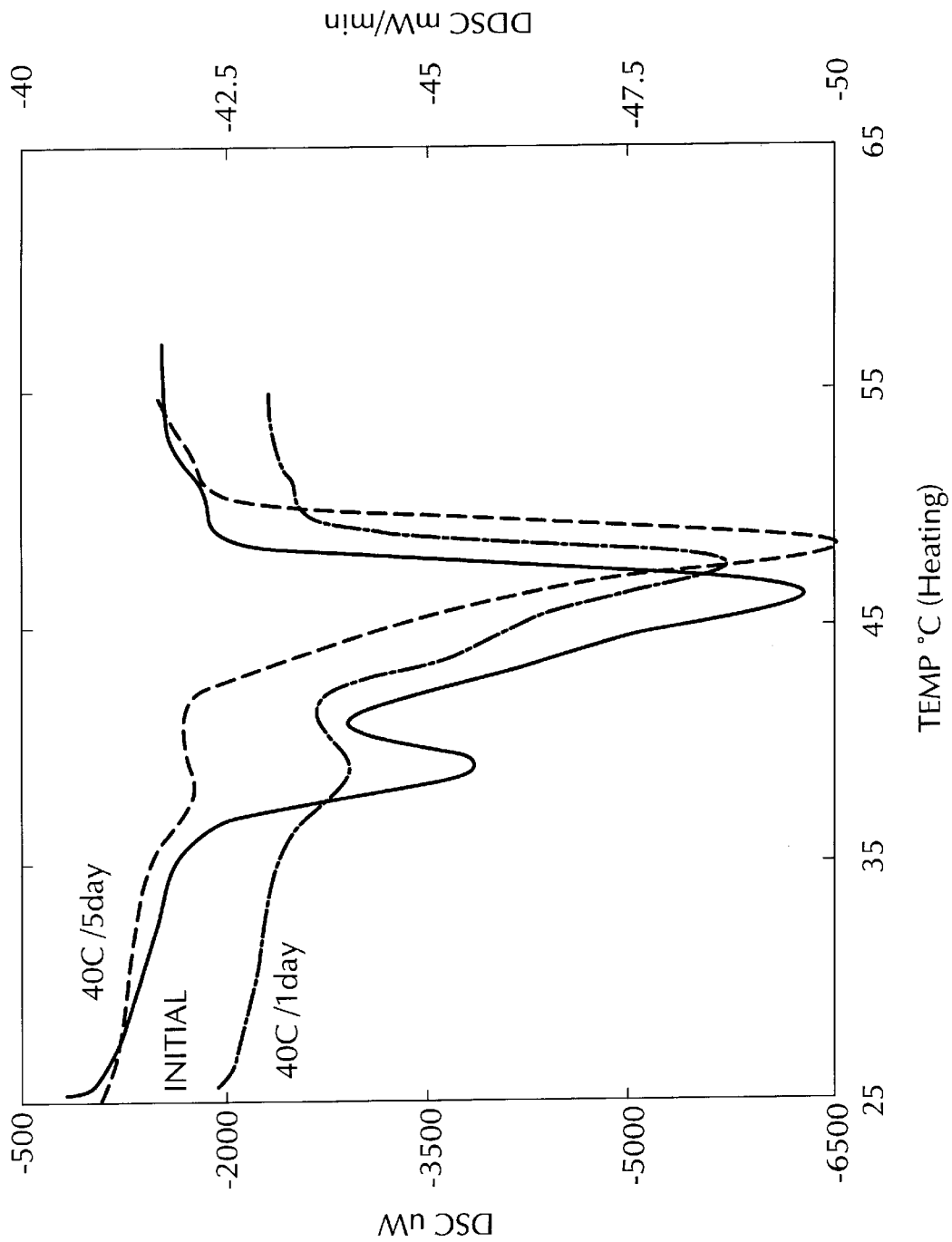
FIG. 4: Gradual conversion of GELUCIRE form I to I' during storage at 40° C.

FIG. 1 represents a typical DSC of the GELUCIRE 50/13-theophylline mixture, where GELUCIRE 50/13 was present in form I, just before the dissolution studies were carried out on freshly prepared capsules. The DSC revealed two characteristic peaks, a premelting transition at approximately 40° C., followed by a larger, perhaps melting, endotherm at 46° C. However, upon storage at 40° C., form I was found to exhibit a similar, but slightly different, DSC curve. The solid form associated with this new DSC was designated as form I' (FIG. 2). The DSC curve of Form I' was found to be very similar to Form I with a premelting transition followed by a larger endotherm. However, the area under the premelting transition was found to be much smaller in form I' compared to form I. Furthermore, the larger endotherm was found to be shifted to a slightly higher temperature (FIG. 3). A gradual conversion of form I to I' when stored at 40° C. is presented in FIG. 4.

Ageing Effects on the Dissolution of Theophylline

Figure 5:
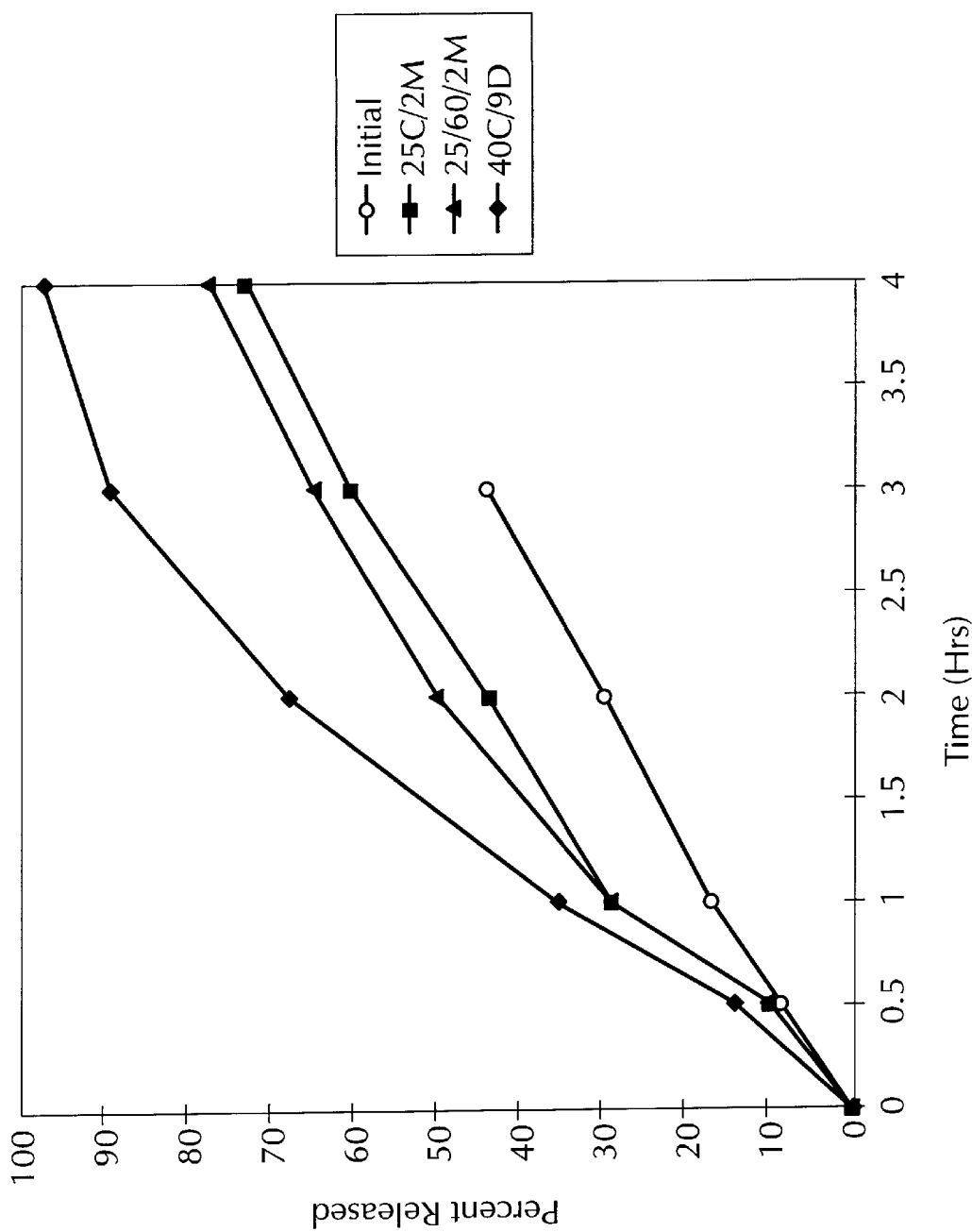
FIG. 5: Effect of ageing on the dissolution of theophylline from theophylline-GELUCIRE 50/13 formulations; initial (open circles); 2 months at 25° C./60% relative humidity ("RH") (closed triangles); 2 months at 25° C. (closed squares); 9 days at 40° C. (closed diamonds).
Figure 6:
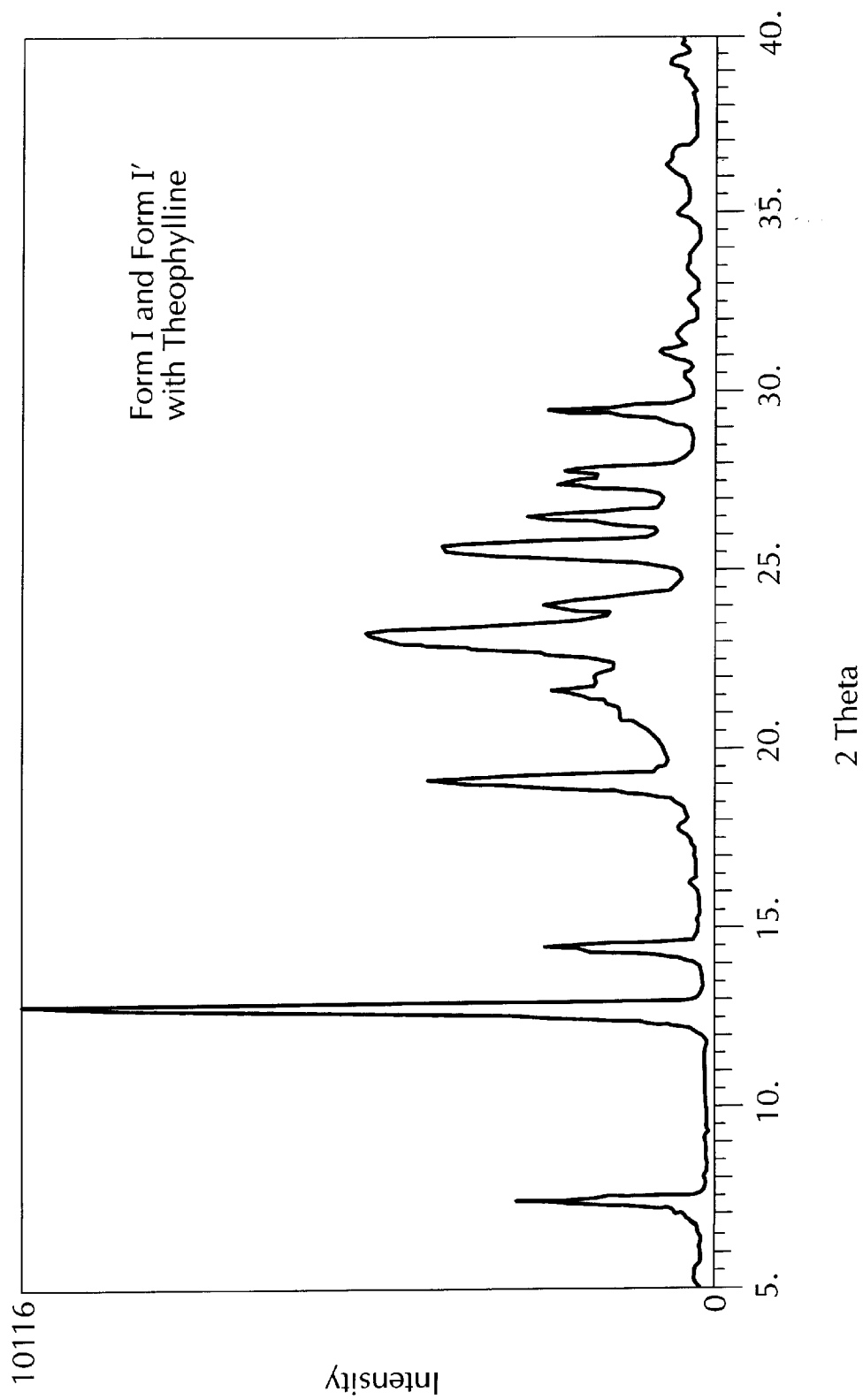
FIG. 6: X-ray diffraction patterns of theophylline-GELUCIRE mixtures prepared fresh (form I) and after storage at 40° C. for 9 days (form I').

Interestingly, storage of the capsules A at 40° C. was also associated with a significant increase in the dissolution rate of theophylline (FIG. 5) and reaches a plateau. The increase in dissolution was significant, but less dramatic, at lower temperatures (e.g. 25° C.). No significant difference in the x-ray diffraction patterns of forms I and I' were observed, suggesting that no gross solid phase transformations (e.g. typical polymorphic or pseudopolymorphic transformations) lead to the conversion of form I to I' (FIG. 6). A dramatic increase in dissolution rate associated with form I to I' conversion warranted a more thorough investigation of the thermal behavior of Form I to explain, and perhaps prevent, the aging effects on the dissolution of theophylline from the GELUCIRE 50/13 matrix.

Hot Stage Microscopy was utilized to understand the nature of the different thermal events observed in the DSC. GELUCIRE 50/13, at room temperature, was found to be crystalline exhibiting significant birefringence under polarized light. When heated to a temperature closer to the premelting transition temperature (40° C.), a slight change in the birefringence was observed, while the solid retained its morphology. Thus, the premelting transition does not appear to be melting of minor components or a eutectic. The solid began to melt at 44° C. At 52° C., although the majority of the wax was found to form a liquid, some intact crystalline portions of the wax were still visible and remained up to 56° C. A separate experiment on a Glyceride-PEG esters mixture suggested that the melting at 44° C. was perhaps related to PEG esters present in GELUCIRE 50/13. Above 52° C., remaining crystalline components in GELUCIRE 50/13 were dissolved by the liquid.

Figure 7:
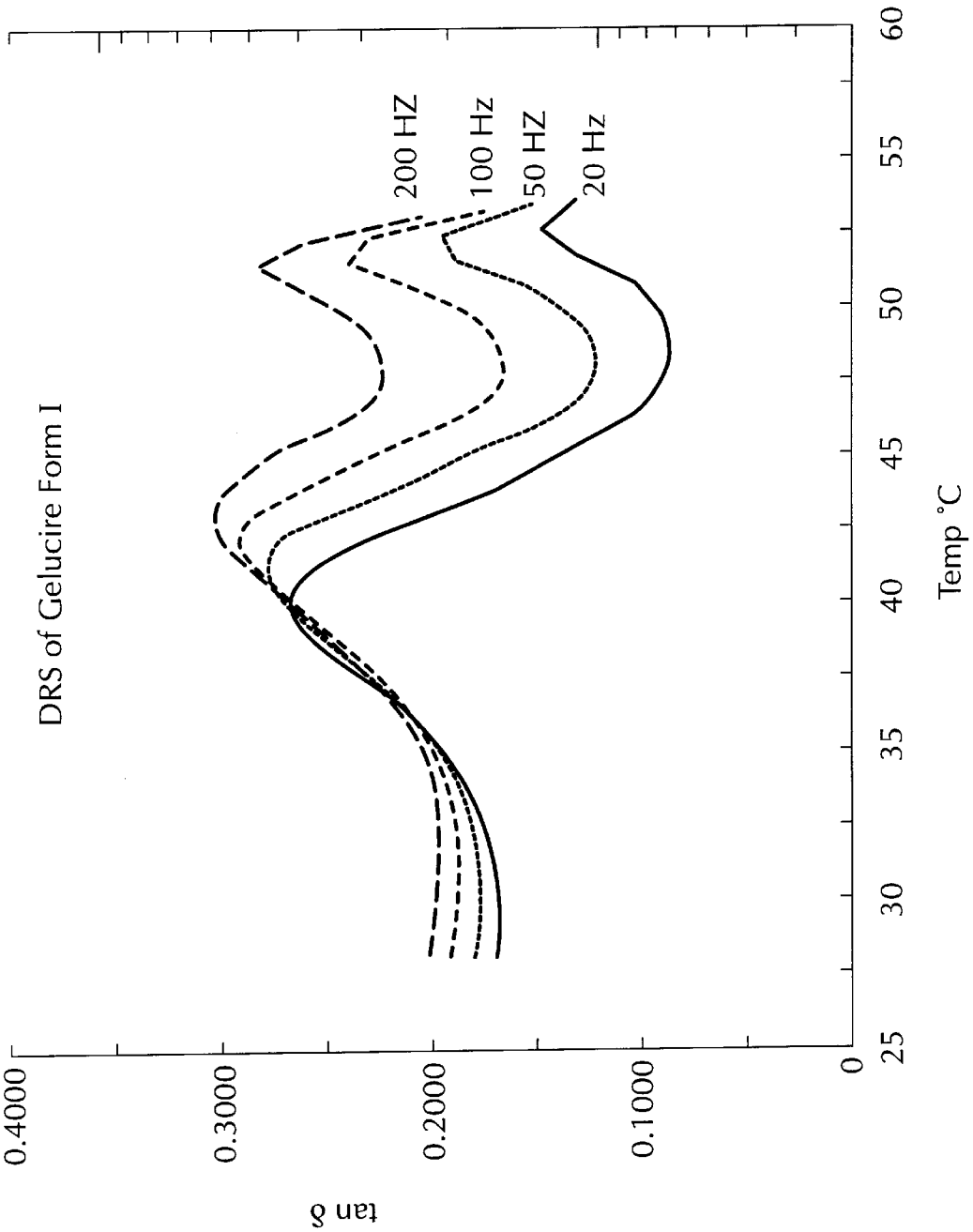
FIG. 7: Dielectric Relaxation spectroscopy (DRS) of GELUCIRE 50/13 form I in the frequency range 20 Hz to 200 Hz. The frequency dependence of the premelting transition suggests that it is a time dependent phenomena.
Figure 8:
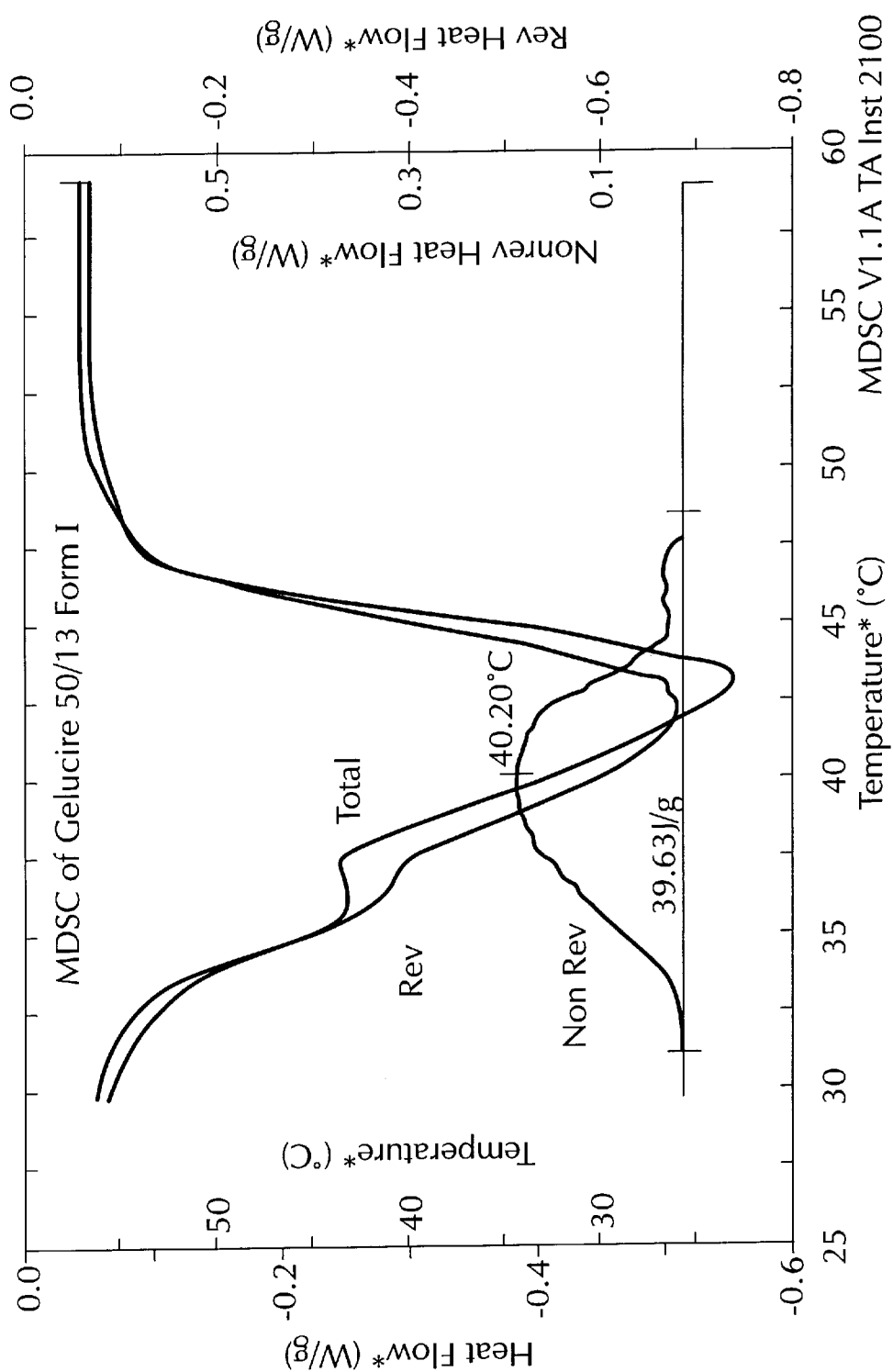
FIG. 8: Modulated DSC (MDSC) curves for GELUCIRE 50/13 form I. The total heat flow signal is deconvoluted into reversing and non-reversing signals, as shown in the figure.

Although the exact nature of the premelting transition was not known at this stage, it was considered vital to the overall conversion of form I to I'. Two new thermal analytical techniques, viz. modulated DSC (MDSC) and dielectric relaxation spectroscopy (DRS), were employed to identify the origin of the premelting phenomena observed in the DSC. DRS (FIG. 7) suggested that the premelting phenomena is frequency dependent (or time dependent) and is perhaps related to an overall change in the mobility of the system analogous to a glass transition in supercooled liquids. Interestingly, MDSC (FIG. 8) indicated that endothermic premelting transition is also associated with a simultaneous exothermic heat event, suggesting a recrystallization process. Thus, the powerful combination of DRS and MDSC revealed far more information than the conventional DSC, suggesting that in characterizing complicated systems, conventional DSC may be of a limited use, and that complementary use of Hot Stage Microscopy, MDSC, DRS may provide a greater insight.

Results from the various characterization studies seem to indicate that the premelting phenomena is associated with a change in molecular mobility followed by recrystallization of one or more components of GELUCIRE 50/13. When the molten mixture was cooled under non-equilibrium conditions, only a fraction of the components crystallized. Thus, the wax was composed of crystalline components along with uncrystallized, supercooled matrix, containing several uncrystallized components, holding the crystals together and or coating the crystals. The supercooled matrix was, however, thermodynamically unstable and eventually underwent a phase separation. Such a phase separation requires an increase in molecular mobility, analogous to a glass transition in supercooled systems. Therefore, the premelting phenomena appeared to be a thermally induced phase separation-recrystallization event. This hypothesis also supports the observation that the conversion from form I to I', and the changes in dissolution are much slower, but significant, at temperatures less than 40° C. Frequency (time) dependent transitions occur over a short time period near the transition temperature and over a longer time period at lower temperatures. Thus, the conversion from form I to I' was expected to be much slower at 25° C. and lower.

Figure 9A:
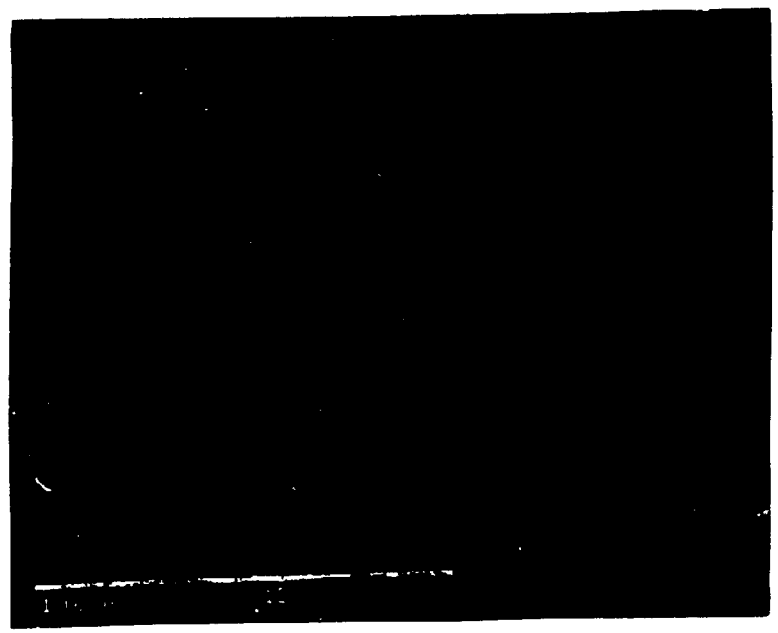
FIG. 9: Scanning Electron Micrographs of GELUCIRE forms I and I', showing gross changes in the morphology following the conversion of form I to I'.
Figure 9B:

A more direct proof of phase separation recrystallization was obtained using the Scanning Electron Microscopy (SEM). As shown in FIG. 9, the SEM of form I indicated a smooth, featureless surface. However, conversion to Form I' was accompanied by the formation of cracks and fissures, creating gaps and spaces on the surface of the wax. Even crystal growth along the cracks can also be observed in FIG. 9, supporting the hypothesis that form I underwent phase separation and recrystallization to produce a more thermodynamically stable form I'. The increase in dissolution was associated with the change from form I to I' because the dissolution medium can more easily penetrate the hydrophobic coating of the wax on theophylline crystals following phase separation due to the large cracks and fissures created. Since phase separation occurs slower at 25° C., the increase in dissolution is slower at 25° C.

It appears that the increase in the dissolution rate of theophylline is associated with a gross morphological change in GELUCIRE 50/13 as a result of thermally induced phase separation and crystallization. The dissolution medium can penetrate the wax coat more easily following the phase separation due to the cracks and gaps created, and dissolve theophylline more easily. The effect of aging on dissolution appears to be dramatic because theophylline is highly water soluble, and even small changes in the wax coating may lead to large changes in the dissolution.

Effect of the incorporation of nucleation enhancers:

Understanding the relation between dissolution and phase separation offers a possible option to minimize the dissolution changes upon aging by preventing phase separation or achieving complete phase separation during the capsule manufacture.

The first strategy of preventing phase separation was a challenging task because of the thermodynamic driving force favoring phase separation. Nevertheless, the potential effect of nucleation inhibitors (e.g., Polyvinylpyrrolidone (PVP), Carboxymethylcellulose (CMC), and Cab-O-Sil) was studied. Each one was added to a GELUCIRE 50/13-theophylline mixture during cooling at a concentration of 5% and 10% w/w, for PVP and 5% of excipient, for CMC 1.25% for Cab-O-Sil, ratio based on the total weight of the excipient. The dissolution profiles of those formulations were monitored after storage at 25° C. and 40° C. For each formulation containing the inhibitor, the dissolution profiles showed a significant change upon aging regardless of temperature, suggesting that this approach may not be useful.

The second approach, consisting of promoting the complete phase separation directly during the manufacturing process, was then explored. Knowing that the phenomena of phase separation and recrystallization was thermally induced, we tried to anneal the capsule at 40° C. to accelerate the phase separation. However, it was found that complete phase separation at 40° C. requires approximately 2 weeks in GELUCIRE 50/13-theophylline mixtures. It was obvious that such a thermal treatment would not be industrially feasible.

As a next step we tried to combine the annealing effect and the addition of an agent to enhance the nucleation during cooling, and hence, facilitating the phase separation. Facilitating phase separation in material such as GELUCIRE 50/13 is not an easy task since GELUCIRE 50/13 is complex in its composition. It is therefore difficult to know exactly which components undergo phase separation upon aging. However it is entirely obvious that the facilitator should be a component of GELUCIRE 50/13. We screened several pharmaceutically acceptable additives, that were of the same general nature as the GELUCIRE 50/13 components and the screened compositions were glyceride monostearate (GMS), PEG 1450, PEG esters mixture, Stearate 1500, and other long chain fatty acids ($C_{16}$, $C_{18}$, $C_{22}$).

Figure 10:
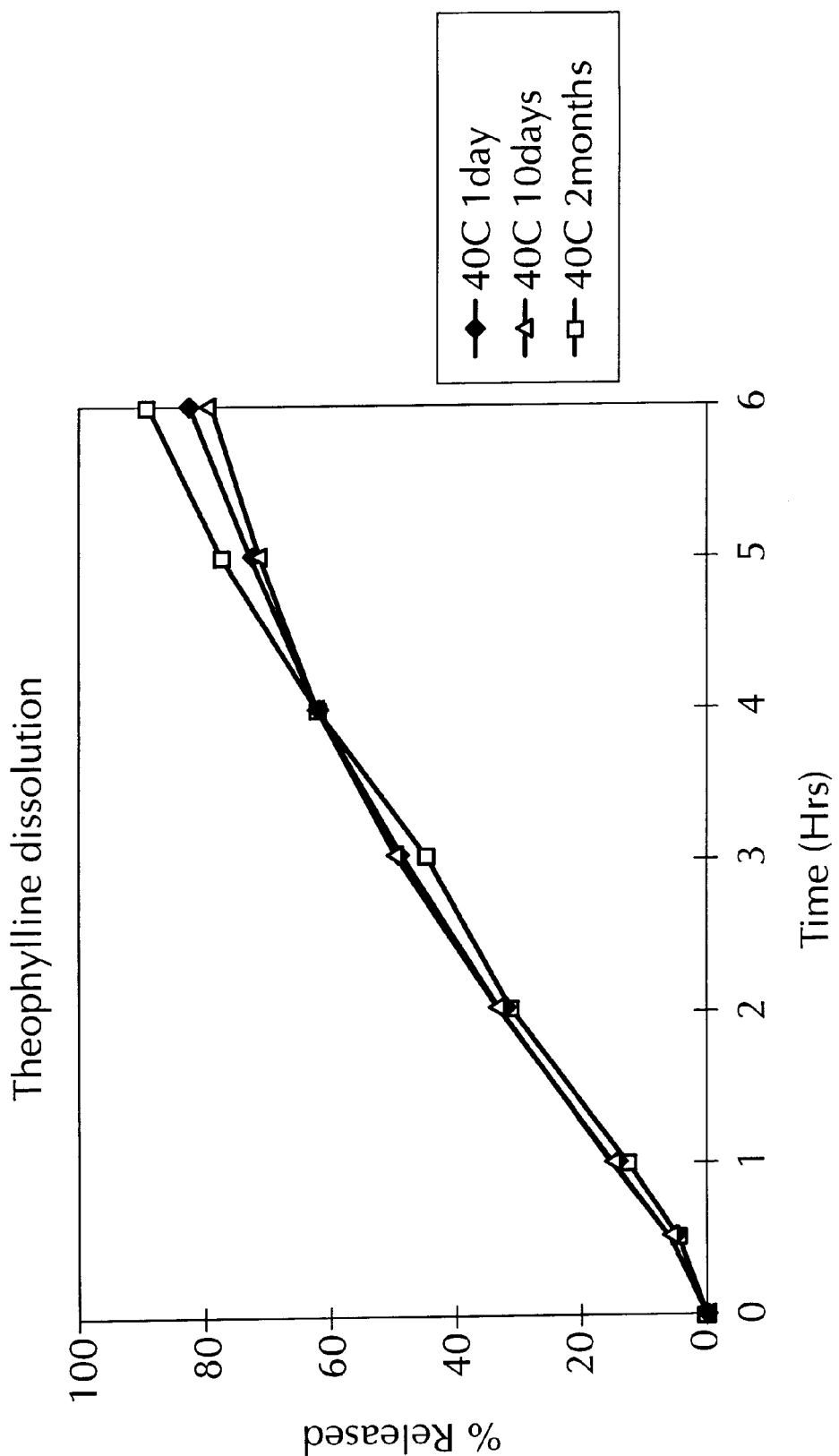
FIG. 10: Effect of ageing upon the dissolution of theophylline from formulations consisting of theophylline, GELUCIRE 50/13 and PEG 1450/GMS.

The components were used at a concentration of 5% w/w of GELUCIRE excipient, and added in the molten mixture at 65° C. before filling and cooling of the capsules. The combination of two of them was also investigated. This excipient screening was performed by monitoring the dissolution profiles changes upon aging (after storage at 25° C. and 40° C. for 1 month). It was determined that the combination PEG 1450 and GMS (5% of each) was very efficient in minimizing the dissolution changes, as shown in FIG. 10. The other approaches failed, and; dissolution profiles increased considerably upon aging.

The combination of PEG 1450 and GMS was studied in a greater detail. Three different concentrations were analyzed 3%, 5% and 8%. 3% appeared to be much less efficient than 5% and 8%, while no significant difference both 5% and 8% was observed. Thus, it is important to have 5% or more of each of those components to facilitate a complete phase separation during the cooling.

Conclusion

By relating physical changes to dissolution increase in rate, it was possible to design a formulation and process to promote complete phase separation during the manufacturing process. A combination of the addition of solid PEG 1450 and solid GMS in the matrix with annealing at 40° C. for 8 hours resulted in virtually no changes in dissolution profiles for up to 2 months when stored at 40° C. Those results were confirmed when two additional batches were prepared using a lower concentration (20%) of theophylline in the formulation (instead of 40%).

What is claimed is:

1. A sustained release theophylline formulation in capsule unit dosage form comprising a gelatin capsule containing a semi-solid matrix, said semi-solid matrix consisting essentially of polyglycolized glycerides, a nucleation enhancer composition consisting essentially of glyceryl mono stearate and polyethylene glycol, and a therapeutically effective amount of theophylline.

2. The formulation of claim 1 wherein the polyglycolized glycerides have a melting point from about 40° C. to about 60° C. and a HLB value from about 10 to about 13.

3. The formulation of claim 2 wherein the nucleation enhancer composition comprises glyceryl mono stearate and polyethylene glycol having a PM from about 1000 to about 2000 in an amount from about 5% to about 50% by weight of the polyglycolized glyceride.

4. The formulation of claim 3 wherein the polyglycolized glycerides is GELUCIRE.

5. The formulation of claim 4 wherein the GELUCIRE has a melting point from about 40° C. to about 60° C. and a HLB value from about 10 to about 13.

6. The formulation of claim 1 consisting essentially of polyglycolized glycerides, a nucleation enhancer composition and a therapeutically effective amount of theophylline.

* * * * *